(12) United States Patent
Strobel

(10) Patent No.: US 6,723,076 B1
(45) Date of Patent: Apr. 20, 2004

(54) ANIMAL DRUG DELIVERY DEVICE

(76) Inventor: Michael Strobel, 1200 S. Hwy. 3, Northfield, MN (US) 55057

(*) Notice: Subject to any disclaimer, the term of this patent is extended or adjusted under 35 U.S.C. 154(b) by 0 days.

(21) Appl. No.: 09/533,783

(22) Filed: Mar. 24, 2000

(51) Int. Cl.$^7$ .............. A61M 5/00; A61B 19/00
(52) U.S. Cl. ................... 604/262; 604/408
(58) Field of Search ............. 604/251, 255, 604/256–262, 403–407, 408–410, 411–415, 905; 222/92, 94, 107, 251, 544, 546; 206/828; 383/41, 67, 904, 906

(56) References Cited

U.S. PATENT DOCUMENTS

| | | | |
|---|---|---|---|
| 4,020,838 A | 5/1977 | Phillips et al. ............ 128/223 |
| 4,090,541 A | 5/1978 | Cammarata, III et al. ... 150/0.5 |
| 4,186,741 A | 2/1980 | Cesaro ................. 128/218 |
| 4,307,766 A | 12/1981 | Tanokura ............... 150/8 |
| 4,308,904 A | 1/1982 | Martin et al. ............. 150/0.5 |
| 4,396,382 A | * 8/1983 | Goldhaber ............... 604/28 |
| 4,641,362 A | * 2/1987 | Muller .................. 383/115 |
| 4,747,834 A | 5/1988 | Prindle ................. 604/184 |
| 4,869,720 A | 9/1989 | Chernack ............... 604/228 |
| 5,154,324 A | 10/1992 | Stratford ............... 222/175 |
| 5,160,320 A | 11/1992 | Yum et al. .............. 604/80 |
| 5,190,534 A | * 3/1993 | Kendell ................. 604/6.16 |
| 5,300,031 A | 4/1994 | Neer et al. .............. 604/154 |
| 5,391,150 A | 2/1995 | Richmond ............... 604/111 |
| 5,405,333 A | 4/1995 | Richmond ............... 604/257 |
| 5,425,528 A | 6/1995 | Rains et al. ............ 251/149.1 |
| 5,647,845 A | 7/1997 | Haber et al. ............. 604/32 |
| 5,683,768 A | * 11/1997 | Shang et al. ............ 428/35.2 |
| 5,733,258 A | 3/1998 | Lane .................... 604/51 |
| 6,039,720 A | * 3/2000 | Wieslander .............. 604/410 |
| 6,071,005 A | * 6/2000 | Ekambaram et al. ........ 366/173.2 |

OTHER PUBLICATIONS

Understanding the Economic Value of Iron, Boehringer Ingelheim, Dec. 1997.

* cited by examiner

*Primary Examiner*—Michael J. Hayes
(74) *Attorney, Agent, or Firm*—Dechert, LLP; John W. Ryan

(57) ABSTRACT

A drug delivery device for holding sterile medicaments, vitamins, nutrients, and the like to animals. The delivery device comprises a flexible sealed bag having at least two attachment points which serve as openings for tubing, at least two flexible lengths of tubing connected to the attachment points of the bag at one end, and adapters attached to an opposite end of each tube wherein said adapters are complementary of one another and detachably connect thereto. A method of filling and using the drug delivery device is also contemplated by the present invention.

4 Claims, 1 Drawing Sheet

ANIMAL DRUG DELIVERY DEVICE

FIELD OF THE INVENTION

The present invention relates to a collapsible apparatus for storing and dispensing fluids. More specifically, the invention relates to a pre-filled, portable, and collapsible bag for the storage and delivery of fluid medications, such as vitamins, vaccines, and nutrients to animals, that is designed to prevent contamination.

DESCRIPTION OF THE PRIOR ART

In administering parenteral medications such as vaccines, vitamins, and nutrients to animals, such as pigs and cattle, it is convenient to have a large reservoir of the medication to facilitate the rapid administration of the medication to many animals. The veterinarian or farmer ("user") uses bottled materials since most of the materials are currently packaged in glass containers. Having obtained the bottled material, the user takes a long needle and inserts the needle into the bottle to extract a desired amount of material. This, however, results in contamination of the whole bottle. In addition, if the needle is introduced to manure or other contaminants, or the needle is not clean or sterile (typically it is not sterile), then the next time the needle is used there is a high possibility that Clostridium, Streptococcus or Staphylococcus could be introduced into the bottle. Clostridium, Streptococcus or Staphylococcus are just three of the common things (virus, contaminants, bacteria, fungi, etc.) in the environment that can be introduced into the bottle. Many other contaminants or diseases can be introduced into the bottle. Once these bacteria or contaminants are located in the bottle, they can grow and cause disease in the animal that was injected with the particular vaccine, vitamin or other material. Therefore, once the traditional bottle systems are opened and used, they will invariably begin to accumulate bacteria growth.

Another method utilizes a dispensing system similar to an IV bag. One disadvantage with the current IV bag systems is that it includes intricate fluid flow mechanisms which require discs and valves to properly regulate the flow of fluids. The high level of sophistication and large number of parts used to regulate the flow of fluid from the IV bags (dispensing systems) can also lead to increased maintenance problems when attempting to interface the systems with syringes or guns.

Another disadvantage is that these systems require the user to take and puncture the primary IV bag, bottle or other means ("material system") with an object such as a syringe or IV simplex. The requirement to puncture a bag, for example, leads to the introduction of contaminants into the bag, thus destroying the sterility of the system.

Another conventional method involves the use of a rigid plastic container that serves as a reservoir to an animal dosing syringe or gun. Examples of dosing syringes and gun can be found in U.S. Pat. No. 4,020,838 to Phillips et al. and U.S. Pat. No. 4,816,741 to Cesaro. Such a container usually holds up to approximately three quarts of medication, which is usually poured into the plastic container and capped with a lid. The container is then connected to the dosing syringe or gun with plastic hosing through the lid of the container or the container itself. Many animals can then be treated with the same needle or dosing apparatus without having to refill the rigid plastic reservoir. Another example is U.S. Pat. No. 5,154,324 to Stratford, which discloses a portable dispensing system for administering fluids to livestock.

Unfortunately, there are many problems with the above-described devices, such as the conventional uses of a rigid plastic reservoir. One problem is that a vacuum is frequently formed in the container because it is typically airtight and the rigid plastic container does not collapse. As the medication is removed from the container, a vacuum is created and the syringe tends to draw air into the container because the passage through the needle constitutes the only vent in the system. As a result, the amount of medication to be administered can be adversely affected. More importantly, air and other contaminants may be inadvertently injected into the animal. Typically materials that are poured into the these containers are of reused medicaments and the like. This leads to undesirable sterilization problems.

A further problem with the use of rigid plastic containers is that they are frequently refilled and reused without proper cleaning. Often at the site at which the inoculation or treatment of the animals is taking place, there is little regard for or effort taken to ensure sanitation, prevent contamination, and promote cleanliness. After the last animal is treated, it is a common practice to leave any left-over medication in the containers until the next use. Thus, future uses of the container may be tainted with medications that have exceeded their shelf life, or if the container is being used to deliver a different medication, the remaining medication may contaminate the newly-added medication and adversely affect the treatment.

A further disadvantage with the use of reusable containers as a reservoir for the delivery of medications to animals is contamination in general. When the containers are refilled at the site of the treatment, impurities from the outside air may contaminate the medications while the container is being refilled. The contamination from outside air can also cause oxidation of the medication over time. This contamination may lead to a greater number of cysts and lesions found on the carcasses after slaughter and a significantly higher risk of injection abscesses and secondary infection, often resulting in death, impaired weight gain, and poor meat quality.

Although some medications are delivered to the user in a sterile form, the transition from the package to the container will compromise the sterility of the medication. Medications are packaged at the pharmaceutical companies in 100 cc–500 cc glass or plastic containers sealed with rubber stopper seals in quantities of usually ten to one hundred doses. At the farm, the user will transfer the medication from the package to the syringe, many times without the use of appropriate sterilization equipment or techniques. Consequently, the medications are easily contaminated by the outside air and non-sterile syringe parts, such as the needles used to pierce the rubber seal of the medication container, the contaminated syringe barrel, the seals at each end, and the plunger of the syringe.

Contamination also occurs during the refilling of the syringe as a contaminated needle is pierced through the rubber seal of the standard medication bottle and a charge of contaminated air is forced into the bottle to provide back pressure to refill the syringe. The user may reinsert the needle into the vaccine bottle five to ten times, for example, for refilling before the bottle is empty. It is not uncommon to vaccinate 100 or more animals with the same needle before switching to a clean needle. The more times the bottle is reentered and the longer the same needle is used, the greater the contamination to the product and to the animals being treated. In addition, cross contamination may occur due to the large number of times the same needle is used. The cross contamination will then cause the rapid spread of many other diseases within herds.

One animal that has been particularly prone to disease resulting from the aforementioned bacteria is the pig. A common parenteral treatment is the administration of iron dextran to pigs. It is well-known that pigs are born with a limited supply of iron (approximately 50 mg) and that a sow's milk contains an inadequate amount of iron (about 1 mg per day) to meet the continuing requirements (7–11 mg per day) of the rapidly growing piglet. The iron deficiency is caused by an imbalance between nutrient needs and availability. Deficiency occurs in nursing pigs due to minimal body stores at birth, low availability from colostrum and milk, confinement rearing and the animals' rapid growth. Without parenteral iron supplementation, signs of deficiency develop because of normal physiological utilization of this element. Thus, piglets need to be injected every 2 to 3 weeks with iron dextran supplements. With such frequent injections, it is important that the injections be accomplished efficiently and without introducing contaminants to the pigs. Moreover, when injecting baby pigs, one will usually only need one-third of the materials. Thus, a system which maintains the sterility of the materials during the use of the materials and the ability to store the remaining, unused materials in a sterile environment is provided.

From the foregoing discussion, it is apparent that there still remains a long-felt, but unfulfilled need to provide an acceptable device which allows a user to carry or transport sterile medicaments to the animals for injection. The fluid storage and dispensing apparatus of the present invention avoids the above-mentioned disadvantages which are characteristic of the prior art.

SUMMARY OF THE INVENTION

The fluid storage and dispensing apparatus of the present invention comprises a flexible, collapsible fluid storage and dispensing apparatus with multiple ports for filling and dispensing fluid to animals. The apparatus does not require the use of discs or valves in order to regulate the flow of fluid from the apparatus to the animal. The apparatus may be connected to a pistol grip syringe or syringe gun for the delivery of fluids to animals.

In addition, the pre-filled bag provides the user with a flexible, collapsible fluid storage and dispensing apparatus with multiple ports for filling and dispensing fluid to animals.

In the preferred embodiments of the present invention, the flexible, sturdy, collapsible fluid storage and dispensing apparatus comprises additional elements that facilitate the convenience, ease of operation and cleanliness of the apparatus.

Numerous objects, features and advantages of the present invention will be readily apparent to those of ordinary skill in the art upon a reading of the following disclosure when taken in conjunction with the accompanying drawings.

DETAILED DESCRIPTION OF THE PREFERRED EMBODIMENT

Figure 1:
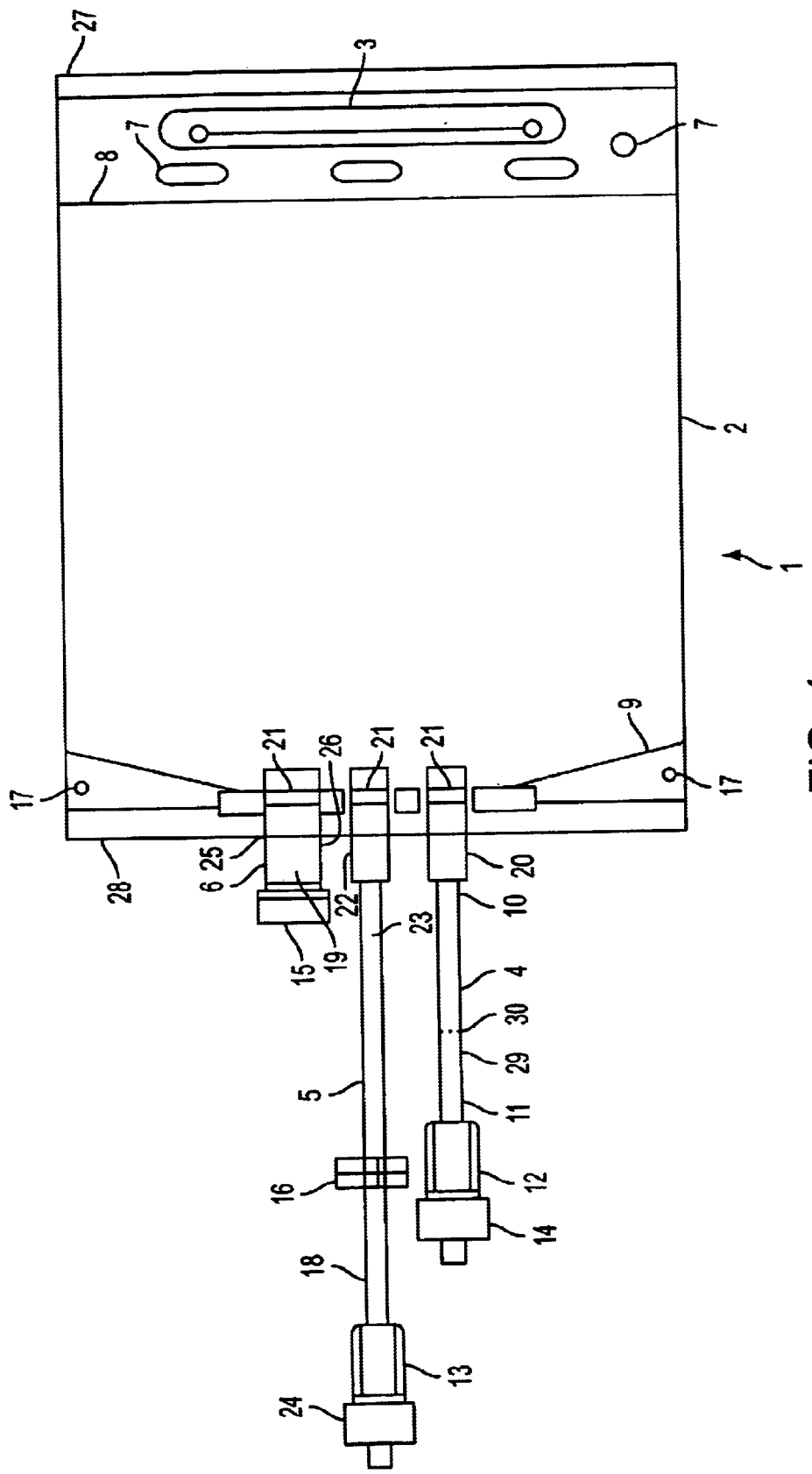
FIG. 1 is a perspective view of the drug delivery bag, including the tubes and stopper which are interfaced with the drug delivery bag.

With reference to FIG. 1 there is shown an animal drug delivery device or "bag system" 1. The bag 2 is lightweight, collapsible and inexpensive. The sealed bag 2 is made of suitable material that is inert and biocompatible. The preferred material is plastic. More preferably, the material is composed of a thick vinyl material. One such plastic material is poly vinyl chloride, manufactured by the Plasco Co., in Chicago, Ill. The material is thicker than conventional vinyl bags so that it will substantially reduce the introduction of air into the bag 2.

Another important feature of the bag 2 is the thick vinyl will hold up better in the field than typical IV bags that are being used today. For example, the thickness and strength of the bag 2 is such that a handle 3 is incorporated into the bag so that the bag 2 can attach to a cart or other holding device.

The thickness of the bag 2 can vary depending on the plastic material that is used. Typically, the thickness of the bag 2 will be between about 6 to about 12 mils. Preferably, the bag 2 has a thickness of about 6 mils. Additionally, the bag 2 will be colored to meet USP specifications so as to prevent light from penetrating the bag 2 and affecting the contents (i.e., fluid) within the bag 2. The bag 2 will typically be opaque.

The bag 2 contains a first end 28 and at least one opening 20, which is configured and dimensioned to receive a tube, such as filling tube 4. The opening 20 is used for the passage of materials into and/or out of the bag 2. The opening 20 can be formed in a multitude of ways. Typically, the opening 20 is formed during manufacture of the bag 2 by standard and well-known techniques (i.e., cutting out a portion of the bag, die cut, etc.). Preferably, filling tube 4 is used for transporting sterile fluid from a port or supply source of desired materials into the bag 2.

Tube 4 has one end 10 connected to opening 20 of bag 2. More preferably, the bag opening 20 is constructed such that it supports the attachment of the tube 4 to the bag 2. This is accomplished by having a rigid like support 21 at the interface between the opening 20 and tube 4. Preferably, support 21 is a thicker portion of the plastic material used to make bag 2. By manufacturing bag 2 with thick supports 21 made of the same plastic material, an additional part that other bags in the art require is eliminated. When manufacturing the bag 2, tubes (4, 5, and 6) are typically heat sealed or solvent sealed to the bag 2. This will cause tube 4 to be permanently fixed into the bag 2 itself. In the alternative, tube 4 is fixedly attached to bag 2 by known means in the art. Preferably, the support 21 is rigid enough to maintain the integrity of tube 4 in opening 20 so that tube 4 will not collapse or cinch in a manner that will constrict the flow of materials from the supply source to bag 2.

At the opposite end 11 of tube 4, there is a detachable complementary adapter 12 for sealing tube 4 from outside contaminants and/or connecting to one of the other tubes. The adapter 12 is such that it has a cap 14 to close adapter 12 from the outside. All the adapters will have a removable cap so as to close off the adapters and maintain the sterility of the system.

Preferably, detachable complementary adapter 12 is attached to tube 4 and will have a male or female part that can optionally interface with another detachable complementary adapter 13. Adapters, 12 and 13, are standard fittings which can be purchased from any number of suppliers. One common manufacturer of such adapters is Qosina. The adapters, 12 and 13, are typically heat sealed to the particular tube. When the caps of the respective adapters 12 and 13 are removed, tubes 4 and 5 are open to the outside environment. This allows adapters 12 and 13 to communicate with one another so that there is a passageway for fluid flow into and out of them so that if desired, the fluid can run through the respective tube and adapter and into the adjacent adapter and tube.

In a preferred embodiment, the detachable complementary adapters 12 and 13 which when inserted into their respective tubes and closed with caps 14 and 24 will prevent air, fluids or other contaminants from entering the particular tube. Ideally, a preferred embodiment of the detachable complementary adapters 12 and 13 will include one adapter with a threaded female opening, while the other adapter will include a threaded male end such that the two adapters 12 and 13 can be connected with one another, via a screwing means. For example, adapter 12 will include a male end and adapter 13 will include a female end. The interface between the two adapters 12 and 13 is such that contamination of the bag 2 will be substantially eliminated.

Although it is possible to only have one opening with one tube attached, it is preferable that the bag 2 will include a second opening 22 which is also fitted with a rigid support 21 to secure and maintain the integrity of second tube 5 in opening 22. The second tubing 5 has first end 23 connected to the bag 2 in opening 22. At an opposite end 18 of tube 5, there is an adapter 13 for communicating with complementary configured adapters. In addition, adapter 13 includes a cap 24 for closing and/or sealing the tube 5 from contaminants. Preferably, this adapter 13 has a fitting whose configuration is such that it can fixedly attach to the fitting of adapter 12. A preferred embodiment of these adapters is a male/female configuration such that the adapters 12 and 13 can be detachably connected to one another by screwing them together.

By including adapters 12 and 13, with connection means (i.e., threaded adapters), tubes 4 and 5 can be connected to one another when the bag 2 is or is not in use. In addition, the connection means allow the user to easily attach the delivery tube 5 to the automatic syringe system.

Similarly, the connecting means allow the user to quickly disconnect the syringe or gun from the bag system 1. This provides a significant advantage over other devices, in that if the whole volume of material in the bag 2 is not used, the bag 2 can be placed back into a storage facility, such as a refrigerator. Moreover, the tubing 5 can quickly detach from the gun without having to detach the tubing 5 from the bag 2. This also allows the user to maintain sterility in the bag system 1 because the fluid is only flowing in one direction, towards the gun or syringe.

A preferred embodiment of the bag system 1 includes a system where the material inside the bag 2 flows unidirectional out of the bag 2, out to the adapter system (male and female adapters 12, 13) and then, into the gun or syringe itself. There are a large number of quality syringe guns on the market, for all injectables (i.e., medicaments) used with poultry, pigs, cattle, sheep, fish, etc. Generally, when using the syringe guns, the doses range from 0.1 ml to 10 ml. One common syringe is the Ovijector. Typically, these guns are one-way systems, where they automatically pull material one dose at a time up to the "injection" system. This embodiment results in a system without back flow. To further insure that there is no back flow, a clamp 16 can be utilized on the delivery tubing 5 that is connected to the injection system for the injection of the desired materials into the particular animal. The injection system is understood to mean the gun or syringe.

Furthermore, clamp 16 is used so that the injection system can be shut off before the injection system is disassembled. Accordingly, when the injection system (gun or syringe) is shut down (i.e., the gun is detached from the bag), clamp 16 will prevent any flow back into the bag 2. This is one of the means for maintaining the sterility of the product in bag 2.

By closing off the bag system 1, there is little or no opportunity for germs, dirt or other contaminants to travel into bag 2. This is one of the many advantages of using a closed system. In the present invention, the user is able to maintain sterility of the product in bag 2 itself since there is no need to puncture the system.

This is particularly important because the present system allows the user to discontinue use of bag system 1 for a period of time and store bag system 1 until needed again. Once the material in bag 2 is needed again, the user can re-assemble the system 1 and use the stored material without compromising the sterility of the system 1. This is a substantial advantage over other systems which are unable to remain sterile. This is particularly important when providing medicine such as vaccinations or vitamins to livestock. Typically when providing medicine to the livestock, the entire contents of the bag 2 are not used at one time. This is routine, for example, when providing iron dextran to baby pigs. Using a bag system 1 that allows the user to only use a portion of the contents is of particular concern for the users. Due to the conservation of materials by using these large bag systems, the user is able to reduce expenses and drastically cut down on the waste that is generally associated with the products currently on the market. Just as important, this invention prevents the contamination of the contents of the bag and this substantially reduces the incident of infection at the site of injection due to use of contaminated products.

Generally, when filling the bag 2 with a particular medicament or fluid, the desired fluid is automatically pumped from a storage container through filling tube 4 and into bag 2. Alternatively, the desired fluid can be introduced into bag 2 by using a hand automated pump to control the flow of material through the filling tube 4 and into the bag 2. Once the sterile fluid is delivered to the sterile bag 2, tube 4 can be heat sealed or clamped so as to keep the contents of the bag 2 in a sterile environment. (See severing/sealing point 30.) After the tube 4 is heat sealed, the remaining portion of tube 4 is severed at a position below the point in which the tube 4 is sealed. The severed section 29 is then attached to the gun or syringe and used as the connecting piece to a second tube 5. This severed section 29 includes adaptor 14, enabling it to be connected to tube 5 when the user is finished using the bag 2, but has remaining medicaments in the bag 2. The user will close tube 5 by first detaching adapter 13 from adapter 12 and then closing adapter 13 with cap 24. Similarly, severed section 29 will be closed by sealing adapter 12 with cap 14. The severed section 29 that is on the syringe is then used when the remaining contents of bag 2 are retrieved from storage.

In addition, once the bag 2 is filled it will reach the user as a pre-filled bag 2. This allows the user to utilize the bag 2 without having to fill the bag 2 before using it, thus eliminating the usual problems associated with adding or filling a medicament bag or bottle out in the field, just prior to when the animal(s) will be injected.

A typical gun/syringe will include a serrated attachment point. The severed portion 29, of tube 4, will then slide over the serrated edge of the injection system, creating a tight and secure fit. Tube 4 will typically have a male adapter 14 which will then connect with the female adapter 13 of delivery tube 5, thus allowing for the gun/syringe to pull one dose of material from the bag 2 at a time.

More preferably, the bag 2 will have a third opening 25 which is configured and dimensioned to receive a first end 26 of tube 6. First end 26 is connected to opening 25 and buttressed by support 21. Although tube 6 may be connected to bag 2 by any means, tube 6 is typically heat sealed or solvent sealed to the bag 2. This will cause the tube 6 to be permanently fixed into the bag 2 itself. Tube 6 has a second end 19 that contains a stopper 15 for preventing contaminants from entering the bag system 1. Preferably, this opening 25 is not utilized since it may compromise the sterility of the bag system 1. Nevertheless, in some situations, the user may need to add additional items to the bag 2, such as additional vaccine or vitamins. This can be accomplished by inserting a syringe or needle through the stopper 15 and discharging the additional vaccine or vitamin into the bag 2. The stopper 15 is configured and dimensioned to interface with the opening 25 in the bag 2 so that the opening 25 is substantially sealed from outside contaminants. Similar to the other openings, it is preferred that opening 25 is constructed by having a rigid like support 21 at the interface between the opening 25 and tube 6 to insure a proper attachment of stopper 15.

Any material may be used for the stopper 15. Preferably, the stopper 15 will be made of a material that allows a syringe to penetrate through the stopper 15 and introduce the desired substances into the bag 2. A preferred material of the stopping device 15 is rubber or similar material (i.e., a rubber stopper).

In a preferred embodiment of bag 2, there is a seam 8 on the opposite end 27 of the bag 2 as openings 20, 21, and 22. The seam 8 separates the fluid storage capability of the bag 2 from a holding means 3 of the bag 2. The holding means 3 (also called a slot) is used for holding the bag 2 in an upright position. Slot 3 is such that there is an ample opening for a hook or similar device which can be positioned through the slot 3, thus maintaining the bag 2 in a desired position.

In a preferred embodiment, the bag 2 will contain a slot 3 and additional opening(s) 7 along the periphery of the bag 2 in order for the device to be hung or attached for support. Although it is not necessary to have openings 7 in the bag 2, one or more holes/openings 7 can serve as additional means to support, position, or hold the bag 2 in a manner desired by the user. Moreover, the holes 7 can serve as a means of attachment to a support when moving the bag 2 to sterilize or treat the animals. In addition, the holes 7 can serve as a means of attachment when storing the bag before or after use.

The slot 3 can be located anywhere within the bag 2. It is preferable if the slot(s) 3 is located on the opposite end 27 of bag 2, away from tubes 4, 5, and 6. This way, the means by which the bag 2 is held or hung for support will be conveniently and safely out of the way from the end 28 where the gun or syringe is connected to the bag 2.

Although not necessary, a seam 9 is on end 28, near the openings 20, 21, and 22 of the bag 2. Seam 9 separates the fluid storage capability from the rest of the bag 2, so that if desired by the user, additional holes 17 can be added to the bag 2. These holes 17 can be used for a variety of means, however, the main use of these holes 17 will be for the user to further secure the bag 2 during use or storage. The holes 17 are of a size sufficient to secure the bag, for example, in a hanging arrangement.

Often times many animals need to be inoculated or provided with minerals and vitamins. Attempting to provide the particular fluid system to a few or large number of animals can take a considerable amount of time. Accordingly, carrying bag 2 around by hand can be very cumbersome, especially for the larger bag systems. The ability to strap bag 2 to a person or attach bag 2 to a more convenient portable means is clearly an advantage over traditional methods of delivering the fluids to animals. For example, securing bag 2 to a vest or pack would allow the user to carry the bag on the user's back. In another means, bag 2 may be secured to a portable apparatus such that the user does not have the strain of carrying bag 2 on his or her person. Furthermore, bag 2 has a capacity large enough so that the user can make numerous injections of the particular animal.

A benefit to the current invention is that it utilizes a system where the gun is attached to a hose or tube 5 which is itself connected to bag 2 that is holding the medicine, vaccine, vitamins etc. If a portion of the contents of bag 2 remains after the user is done treating the animal, the user can disengage tube 5 from the gun and place bag 2 in a storage facility, such as a refrigerator, and then retrieve the system when the need arises.

The size of the bags will also vary. Bag systems can comprise many different sizes, for example, ranging from about 1,000 ml to about 5,000 ml units. The typical bag system can hold around 2000 milliliters of material. However, the capacity of the bag systems will vary depending on the dosage necessary and the number of livestock. Any number of materials can be placed inside the bag. The desired materials may include any number of vaccines, medicaments, or vitamins that are necessary for the particular animal. Some materials include iron dextran, ampicillin, gentocin, B Vitamins, and many others.

While the preferred embodiments of the invention have been particularly described in the specification and illustrated in the drawings, it should be understood that the invention is not so limited. Many modifications, equivalents, and adaptations of the invention will become apparent to those skilled in the art without departing from the spirit and scope of the invention as defined in the appended claims.

I claim:

1. A method of preparing a device for holding liquids, comprising:

filling a bag with sterile liquid medicaments to a desired level through a tube that is connected to the bag at an attachment point; and sealing the tube such that the tube is sealed from the outside environment to prevent any contamination of the liquid medicaments;

cutting said tube after sealing the tube;

attaching a cut portion of the tube to a gun or syringe; and connecting the cut portion of the tube to a second tube that is attached to the bag.

2. The method of preparing the device for holding liquids in claim 1 wherein the bag is filled with the liquid medicaments using an automated system.

3. The method of preparing the device for holding liquids in claim 1 further comprising:

attaching the bag to a cart thereby increasing the mobility of the bag.

4. The method of preparing the device for holding liquids in claim 1, wherein the liquid medicament is iron dextran.

* * * * *